United States Patent [19]
Reeder et al.

[11] Patent Number: 5,370,111
[45] Date of Patent: * Dec. 6, 1994

[54] MOBILE VENTILATOR CAPABLE OF NESTING WITHIN AND DOCKING WITH A HOSPITAL BED BASE

[75] Inventors: Ryan A. Reeder; Leslie D. Foster, both of Brookville, Ind.

[73] Assignee: Hill-Rom Company, Inc., Batesville, Ind.

[*] Notice: The portion of the term of this patent subsequent to Jun. 2, 2009 has been disclaimed.

[21] Appl. No.: 874,586

[22] Filed: Apr. 24, 1992

Related U.S. Application Data

[63] Continuation-in-part of Ser. No. 524,038, May 16, 1990, Pat. No. 5,117,521.

[51] Int. Cl.$^5$ .............................................. A47G 21/00
[52] U.S. Cl. .......................... 128/202.13; 128/202.27; 128/204.18; 248/129; 5/510; 5/503.1; 5/658; 296/20
[58] Field of Search ............ 128/202.13, 200.24, 128/202.27, 204.18; 5/1, 2.1, 503.1, 510, 620, 600, 658, 507.1; 248/121, 125, 129; 296/19, 20

[56] References Cited

U.S. PATENT DOCUMENTS

| | | | |
|---|---|---|---|
| 2,039,901 | 5/1936 | Hawley | 128/204.18 X |
| 2,607,929 | 8/1952 | Balluff | 5/618 |
| 2,847,006 | 8/1958 | Griffith | 128/202.13 |
| 3,281,103 | 10/1966 | Kisling | 248/132 |
| 3,524,512 | 8/1970 | Voeks et al. | 180/14.1 |
| 4,578,833 | 4/1986 | Vrzalik | 5/607 |
| 4,584,989 | 4/1986 | Stith | 128/1 D |
| 4,894,876 | 1/1990 | Fenwick | 5/602 |
| 4,944,292 | 7/1990 | Gaeke | 128/204.18 |
| 4,945,592 | 8/1990 | Sims | 5/508 |
| 4,953,243 | 9/1990 | Birkmann | 5/600 |
| 4,957,121 | 9/1990 | Icenogle | 128/897 |
| 4,966,340 | 10/1990 | Hunter | 248/125 |
| 4,985,946 | 1/1991 | Foster et al. | 5/601 |
| 5,022,105 | 6/1991 | Catoe | 5/11 |
| 5,042,470 | 8/1991 | Kanesaka | 128/202.22 |
| 5,054,141 | 10/1991 | Foster et al. | 5/611 |
| 5,072,906 | 12/1991 | Foster | 248/122 |
| 5,117,521 | 6/1992 | Foster | 5/510 |
| 5,117,819 | 6/1992 | Servidio | 128/204.18 |

FOREIGN PATENT DOCUMENTS

| | | | |
|---|---|---|---|
| 2285113 | 4/1976 | France | 296/20 |
| 2818189 | 6/1979 | Germany | 5/503.1 |
| 2812037A | 9/1979 | Germany | |
| 2153771 | 8/1985 | United Kingdom | 296/20 |

Primary Examiner—Edgar S. Burr
Assistant Examiner—E. P. Raciti
Attorney, Agent, or Firm—Wood, Herron & Evans

[57] ABSTRACT

A hospital bed supported on a wheeled base, and a ventilator supported on a wheeled cart and docked to the base of the bed, the combination of ventilator and bed capable of being rolled as a single unit. The ventilator cart includes a wheeled base, and supports connected to the base for supporting a ventilator, with the supports providing for selective raising and lowering of the ventilator. The hospital bed base is wheeled and has a generally Y-shaped base frame. The outspread arms of the Y-shaped base frame receives the ventilator cart so that the two may be docked together. The ventilator when docked to the hospital bed base falls within the footprint of the bed as projected downwardly onto the floor. A latch secures the ventilator to the bed base. A disabling switch disables the high/low function of the bed preventing the bed from being lowered downwardly onto the ventilator. A power supply mounted to the bed base provides for uninterrupted operation of the ventilator.

17 Claims, 3 Drawing Sheets

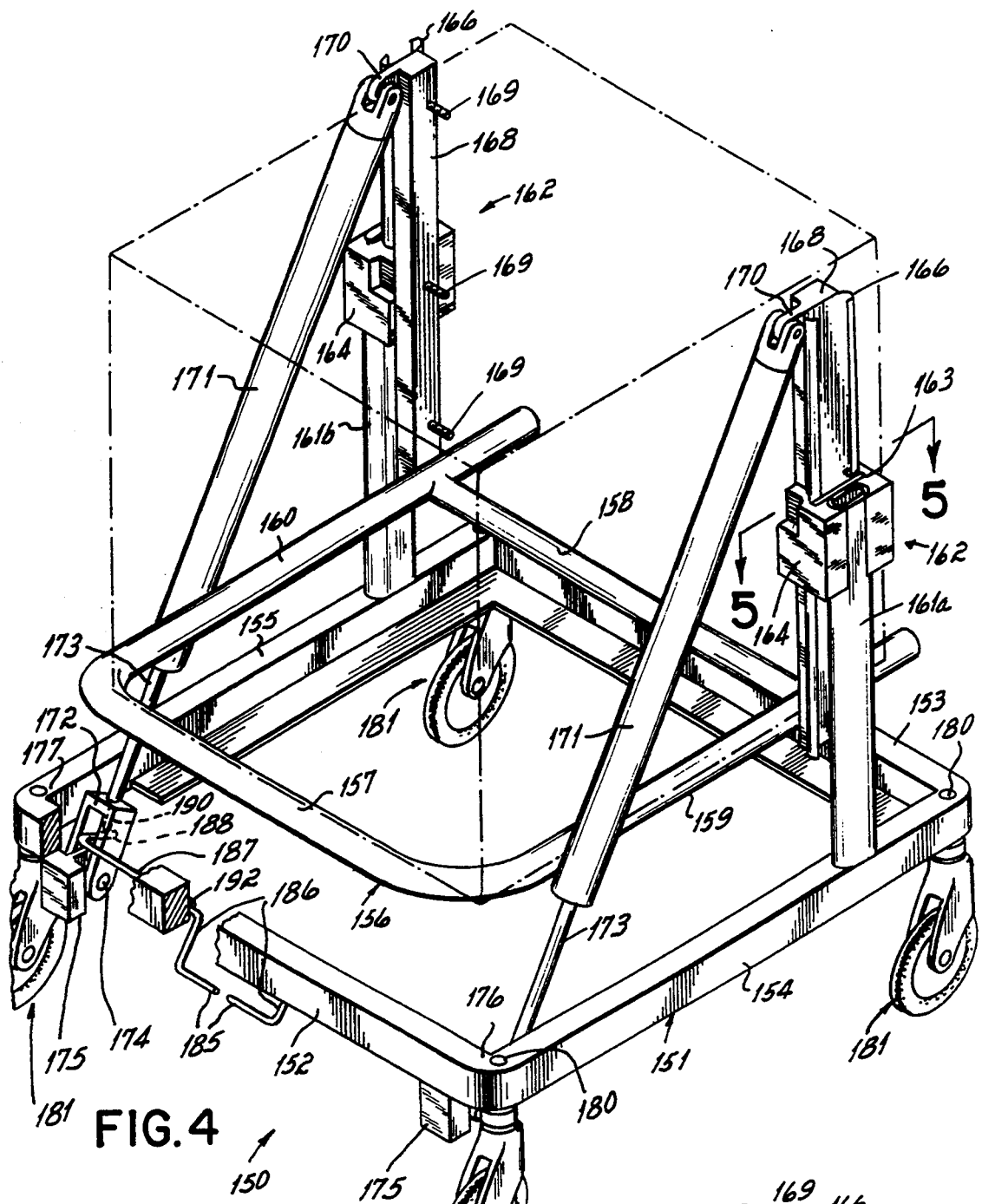
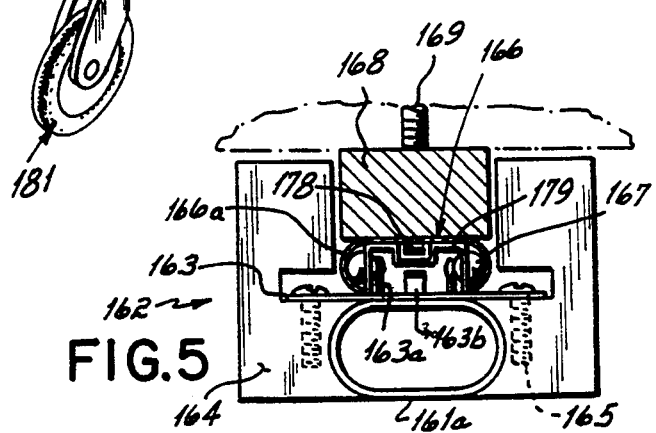
FIG. 4
FIG. 5

MOBILE VENTILATOR CAPABLE OF NESTING WITHIN AND DOCKING WITH A HOSPITAL BED BASE

This application is a continuation-in-part of co-pending U.S. application Ser. No. 07/524,038 entitled Care Cart And Transport System filed May 16, 1990, now U.S. Pat. No. 5,117,521 having issued Jun. 2, 1992.

FIELD OF THE INVENTION

This invention relates generally to medical equipment, and more particularly to the integration of patient life support systems into the dimensions of a hospital bed. More specifically, this invention relates to patient ventilators and carts for supporting ventilators in combination with hospital beds for movement with the beds.

BACKGROUND OF THE INVENTION

The patient critical care environment in hospitals is becoming increasingly crowded due to the number of pieces of medical equipment associated with critical care, which pieces of equipment embody various critical care technologies. Specifically, within the critical care environment there is generally located a critical care bed, around which are positioned a ventilator, I.V. pumps, various monitors, and one or more computer terminals for entering patient care data. The numerosity of pieces of equipment spaced about a critical care hospital room and the patient bed results in patient care inefficiency, as a care provider must continually monitor and operate all the pieces of equipment, while such are not advantageously ergonomically arranged.

In addition to the critical care environment being crowded and somewhat cumbersome around which to work, the transfer of the various pieces of equipment along with the patient on the critical care bed from one room to another within the hospital is tedious, time consuming and difficult to manage. One reason is that the critical care bed, and the various technologies associated with the critical care environment, are generally each individually supported on wheeled support structures. Therefore, when transferring the patient from one room to another room, several pieces of wheeled equipment must simultaneously be rolled to the new location. Not only is this task cumbersome, but also it is time consuming. Further, since all the various technologies must be first disconnected from their respective connections to AC power at the wall in the room, the various technologies must either operate on some sort of standby scheme during transportation, or must be manually operated. Swift transfer of the various pieces of equipment with the critical care bed from one room to another is mandatory in order to minimize down time on these pieces of equipment yet is made very difficult by the clutter associated with the several individual pieces of equipment.

SUMMARY OF THE INVENTION

In accordance with the principles of this invention, a significant improvement in patient critical care and movement is made by consolidating the patient ventilator required in a typical critical care environment not only for its stationary use but also for transportation purposes as well. That is, rather than rolling the patient ventilator along with the patient bed from one room to the next, the present invention enables a hospital worker to roll, as a single unit, both the bed and the ventilator as a single, integrated critical care unit.

The typical critical care bed is manufactured to certain external dimensions to enable the bed to be rolled, for example, through doorways, down aisles, and into elevators. The external dimensions of the bed are referred to as the bed's "footprint". Hospital workers are familiar with maneuvering such a standard critical care bed within this footprint. The present invention combines movement of the ventilator with the critical care bed within this footprint in such a manner that the outer dimensions of the critical care bed are not exceeded, thereby taking advantage of the fact that the bed has been designed to freely travel down aisles, through doors and the like, and of the familiarity of the hospital worker with maneuvering the critical care bed.

The patient ventilator which normally stands in a position next to the bed is in accordance with this invention capable of being quickly and efficiently locked within the patient bed base and within the bed footprint for rolling movement with the bed from one location to another.

Since the ventilator must be disconnected from its source of AC power at the hospital room wall before transferring it to a new room, this invention provides for powering the ventilator directly by the bed itself. This eliminates any down time of the ventilator thereby providing for uninterrupted operation of the ventilator during movement of the patient and patient bed.

The present invention provides a hospital bed supported on a wheeled base, and a ventilator supported on a wheeled cart which may be docked to the base of the bed, the combination of ventilator and bed capable of being rolled as a single unit within the bed footprint.

The ventilator cart of the present invention includes a wheeled base, and supports connected to the base for supporting a ventilator, with the supports providing for selective raising and lowering of a ventilator supported by the supports. The ventilator cart provides for positioning the ventilator in a high position for operating the ventilator next to a patient bed and in a low position for docking the ventilator to the hospital bed base beneath a bed mounted on the base.

The hospital bed base is wheeled and has a generally Y-shaped base frame. The outspread arms of the Y-shaped base frame receive the wheeled ventilator cart in its lowered position such that the two may be docked together. The ventilator when docked within the outspread arms of the Y-shaped base frame of the hospital bed base falls within the footprint of the bed as projected downwardly onto the floor.

A mechanical latch is employed to secure the ventilator to the hospital bed base. The latch cooperates with a disabling switch which disables the high/low function of the bed mounted on the bed base, thereby preventing the bed from being lowered onto the ventilator. The disabling switch may be of the optical, mechanical or ribbon type.

A power supply is mounted to the hospital bed base, and plugs into the ventilator when the ventilator is docked to the bed base, thereby providing for uninterrupted operation of the ventilator when transferring the ventilator from one room to another room.

One advantage of the present invention is that transportation of a critical care bed and the patient ventilator from one hospital room to another is facilitated. The docking of the ventilator to the bed base is quickly and easily accomplished thereby saving time when time may be critical to the patient.

Another advantage of the present invention is that the physical packaging associated with a critical care bed and its ventilator is reduced, as the ventilator has the ability to nest within and dock with a hospital bed base underneath and within the footprint of the bed and to move with the bed within its footprint.

Yet another advantage of the present invention is that a ventilator is able to operate in an uninterrupted manner when moving the ventilator with a bed from one hospital room to another hospital room.

BRIEF DESCRIPTION OF THE DRAWINGS

FIG. 4 illustrates another embodiment of the ventilator cart of the present invention; and FIG. 5 is a view taken along line 5 of FIG. 4.

Figure 1:
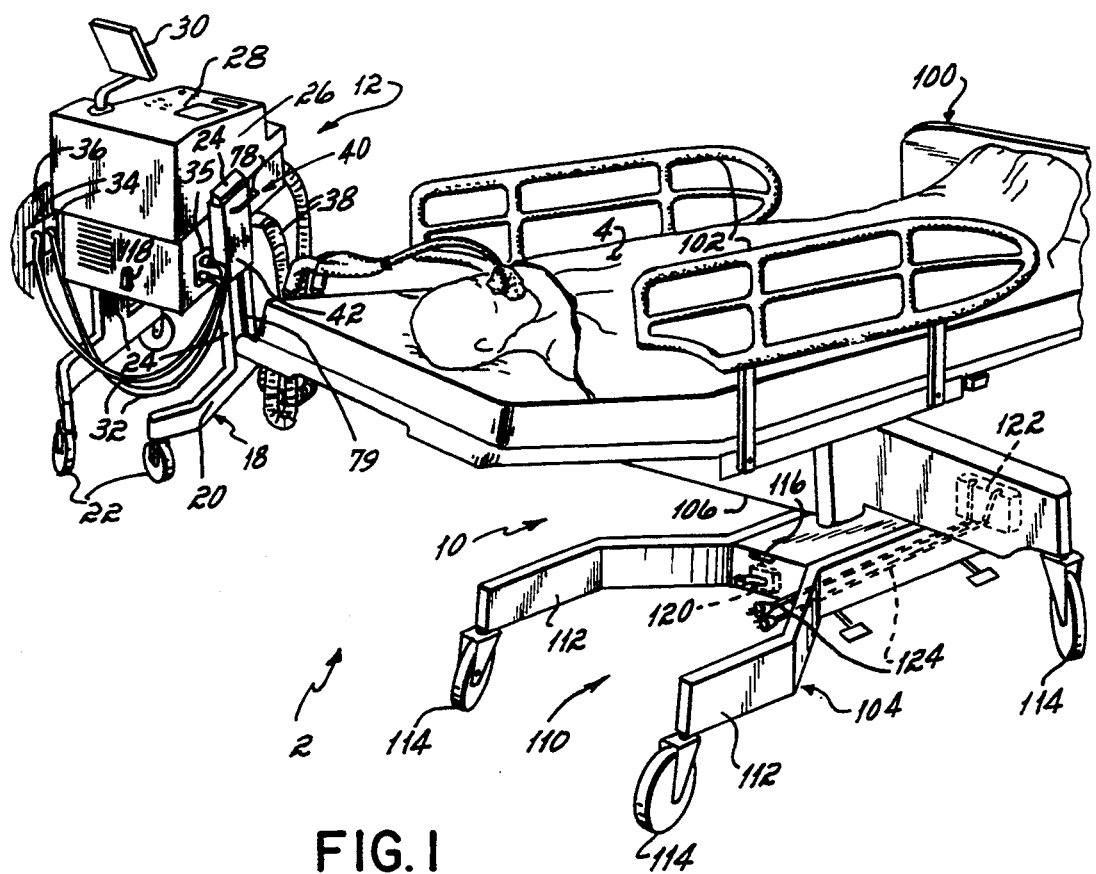
FIG. 1 is a perspective view of the present invention with the ventilator in its high position and separated from the hospital bed base and connected to AC wall outlets.
Figure 2:
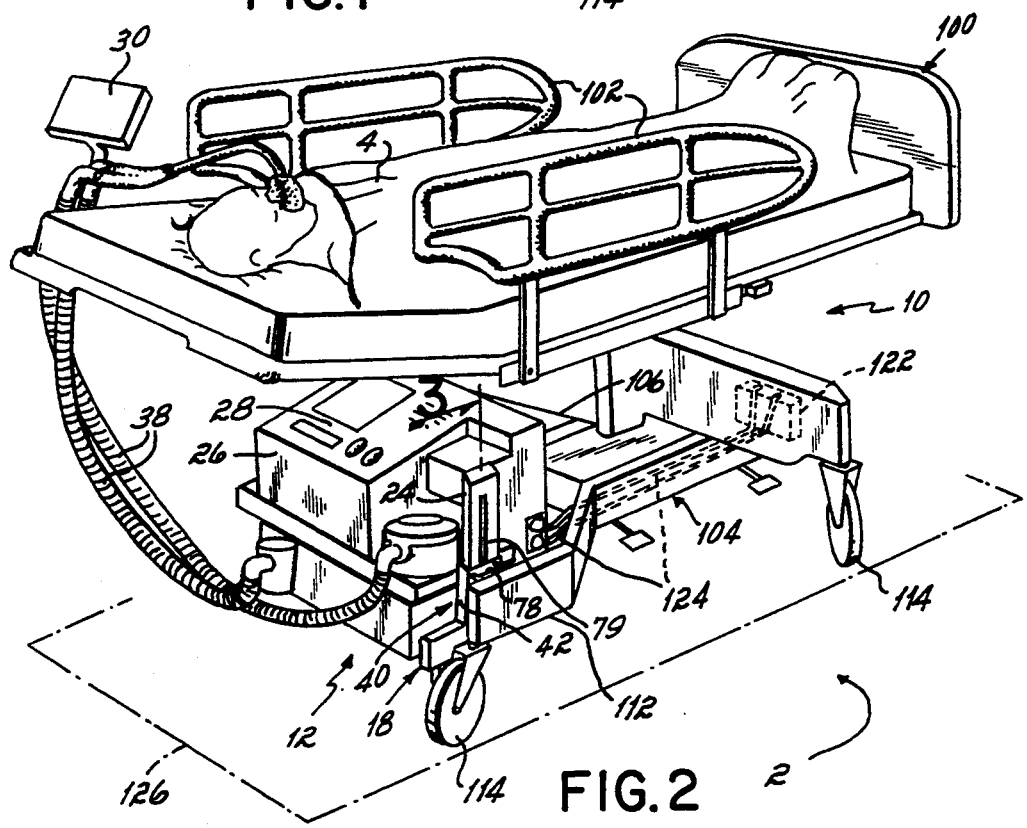
FIG. 2 is a view similar to FIG. 1 but illustrating the ventilator in its low position and docked to the hospital bed base and powered by the bed power supply.

With reference to the drawings, and first to FIGS. 1 and 2, there is illustrated a critical care environment designated generally by the numeral 2 for providing care to a critically ill patient 4. The standard critical care environment 2 includes, generally, a critical care bed assembly 10, and a mobile ventilator assembly 12. Other critical care equipment such as I.V. pumps, various monitors, and one or more terminals for entering patient care data, are also typically present in this environment but are not shown in the drawings for clarity purposes.

The mobile ventilator assembly 12 includes a ventilator cart 18 having a base 20 to which are mounted wheels or casters 22. Extending upwardly from the base 20 are a pair of uprights 24, 24 for supporting a ventilator 26. The ventilator 26 includes a control panel 28 and a flat panel display 30 for monitoring the ventilator 26. The ventilator 26 includes cables 32, 32 to supply power from suitable AC outlets 34, 34 mounted on a wall 36 of a critical care hospital room. The ventilator 26 is tethered to the patient 4 via hoses 38, 38.

Referring to FIG. 1, the ventilator 26 is illustrated in its upwardmost position where it is approximately bedside height thereby facilitating operation of the ventilator 26 by a care provider by placing control panel 28 and display 30 at a convenient height.

Figure 3:
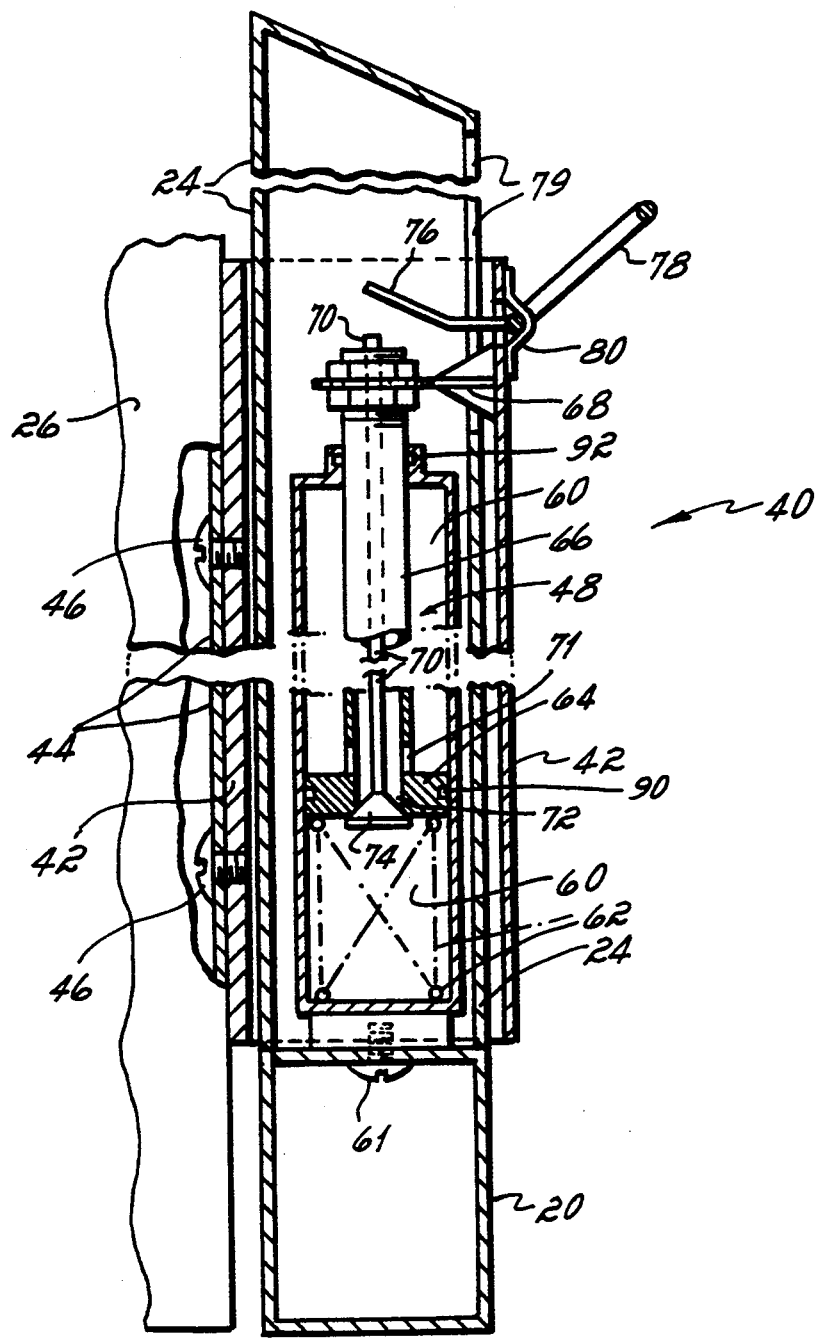
FIG. 3 is a schematic view taken along line 3 of FIG. 2 and illustrating one mechanism for raising and lowering the ventilator on the ventilator cart, the mechanism being shown in a lowered position.

With reference to FIG. 2, it will be noted that the ventilator 26 is lowered and positioned in a downwardmost compact configuration in order to be docked with the critical care bed assembly 10 for transporting both the bed assembly 10 and ventilator assembly 12 as a unit. In order to raise and lower the ventilator 26, each support 24 is provided with an adjusting mechanism 40 which allows for selectively raising and lowering the ventilator 26 on the supports 24. While most any suitable mechanism 40 could be utilized, one such adjusting mechanism is illustrated in FIG. 3. Each mechanism 40 includes a generally box shaped sleeve 42 mounted for vertical sliding movement on its respective support 24. The sleeve 42 is fixedly secured to an external wall 44 of the ventilator 26 as by screws 46. Mounted internally of the support 24 is an air spring assembly 48. Air spring assembly 48 includes an elongated air tight plenum 60 fixedly secured by bolts 61 to the base 20 of cart 15. A coil spring 62 resides in the bottom of the plenum 60 and provides assistance in lifting the weight of the ventilator 26 when adjusting the ventilator from the low position to the high position. The coil spring 62 acts upon a block or piston 64 which is fixedly secured to the lower end of a hollow cylinder or piston rod 66. The upper end of cylinder 66 is connected to the sleeve 42 via a bracket 68. Contained within the cylinder 66 is a rod 70 which extends downwardly through an aperture 72 in the block 64 and has on its lower end a valve 74 which seats against the lower side of the block 64. The upper end of rod 70 is adapted to be moved vertically by a pivotable lever 76 which itself is an extension of a handle 78 mounted to sleeve 42 via a bracket 80. To facilitate this vertical movement of sleeve 42 and hence lever 76, the uprights 24 have a vertical slot 79 through which the bracket 68 extends.

Block 64 includes around its periphery a suitable seal 90 to prevent air from transferring between the two cavities of plenum 60 defined by the block 64. A seal 92 is utilized at the upper end of plenum 60 to allow the cylinder 66 to travel vertically with respect to the plenum 60 without loss of air therefrom.

It will be appreciated that upward motion of handle 78 causes downward motion of lever 76, the end of which contacts the upper end of rod 70. Continued upward motion of handle 78 causes the lever 76 to force rod 70 downwardly causing valve 74 to unseat from the lower surface of block 64. Rod 70 is spring loaded with respect to cylinder 66 internally by means not shown, such that when handle 78 is released, lever 76 rises thereby releasing rod 70, which then returns to its normal state with valve 74 seated against the lower surface of block 64. The handle 78 may, if desired, also be spring biased to a released position shown but it is anticipated that the weight of handle 78 will overcome the weight of lever 76 and release itself by gravity.

When handle 78 is raised upwardly thereby depressing the upper end of rod 70 downwardly by virtue of the lever 76, it will be appreciated that air may freely travel through ports 71 in cylinder 66 and aperture 72 in block 64 to equalize the volume of air on both the upper and lower sides of the block 64. As handle 78 is additionally raised upwardly, sleeve 42 slides upwardly on post 24 and cylinder 70 and block 64 slide upwardly within plenum 60. Air volume is thereby equalized on either side of the block 64. When the ventilator 26 has been moved into its desired upward position, handle 78 is released, thereby causing valve 74 to reseat, the volume of air trapped therebelow by virtue of block 64 and seal 90 preventing the weight of the ventilator 26 from moving it downwardly. Of course, the force of coil spring 62 aids in overcoming the weight of the ventilator 26 when raising same, and must be overcome by downward force on the ventilator 26 when moving same downwardly.

Many other devices and mechanisms could similarly be employed to raise and lower the ventilator 26 on supports 24, and the invention is not limited to the specific embodiment illustrated, as same is only for illustrative purposes. Furthermore, such a device or mechanism could as easily be foot operated rather than hand operated.

Referring back now to FIGS. 1 and 2, the critical care bed assembly 10 includes a bed 100 with appropriate side guards 102, mounted onto a bed base 104 with suitable supporting structure 106, shown schematically. Bed base 104 includes a generally Y-shaped base frame 110 which includes outspread arms 112, 112 and wheels or casters 114 mounted to the ends of the outspread arms 112, 112 and to the opposite end of the base frame 110. The outspread arms 112, 112 are adapted to receive the mobile ventilator assembly 12 therein, when the ventilator assembly is in its lowered compact configuration, as is illustrated in FIG. 2.

A suitable mechanical latch 116 is located generally within the trough area of the outspread arms 112, 112 and is employed for removably securing the mobile ventilator assembly 12 to the bed base 104. A suitable cooperating latch mechanism 118 is located on the rear side of the ventilator 26 in a suitable location to mate with bed latch 116 when the ventilator assembly 12 is at the lowered position of FIG. 2. While the cooperating latch 118 is illustrated as being mounted to a cross piece (not shown) of the ventilator 26, it could just as easily be mounted to a cross-piece (not shown) of the base 20 of the ventilator cart 18.

The bed 100 mounted to the bed base 104 generally includes suitable electrical controls for varying the height of the bed 100 above a floor surface by changing the attitude of the supporting structure 106. In order to prevent the bed 100 from being lowered onto the mobile ventilator assembly 12 when same is docked to the bed base 104, there is provided with the latch 116 a suitable switch 120 for disabling this high/low function of the bed 100. Most any suitable switch 120 could be utilized, and could be of, for example, the optical, mechanical or ribbon type.

To provide for uninterrupted operation of the ventilator 26, a suitable DC power supply 122 is provided. While the power supply 122 could be contained within the ventilator 26, mounted to the ventilator cart base 20, or could even be a part of the bed supporting structure 106, it is preferably mounted to the bed base 110. Suitable cables 124 connect the power supply 122 to the ventilator 26. Ideally, connecting cables 124 to the ventilator 26 would immediately internally to the ventilator 26 disconnect the AC power provided by the AC outlets 34 and immediately switch the ventilator over to DC power supplied by the power supply 122. Cables 32 could then be unplugged from their respective AC ventilator outlets 34 thereby providing for continuous operation of and elimination of any downtime associated with the ventilator 26 during transportation of the bed assembly 10 and ventilator assembly 12 to another location.

Referring to FIG. 2, it will be noted that the periphery of the bed 100 when projected downwardly onto the floor therebelow defines a footprint 126. As can be seen, in the nested configuration, the mobile ventilator assembly 12 falls well within this footprint 126. Therefore, a hospital care provider normally adept at maneuvering the critical care bed assembly 10 need not have to account for a larger footprint in maneuvering the combination through doors, down aisles and into elevators. The care provider can simply maneuver the critical care bed assembly 10 as before, and without the necessity of individually rolling the mobile ventilator assembly 10 therebeside when transferring the equipment from one hospital room to another. Furthermore, the need to hurriedly transfer the equipment from one room to another and hence from one wall AC source to another wall AC source is eliminated.

Other variations of a combination hospital bed and ventilator are contemplated by the invention. For example, the ventilator could be separated from its wheeled cart and docked to the hospital bed base, to the supporting structure which mounts bed to base, or even the hospital bed itself underneath a head section thereof. All such variations would provide a hospital bed-ventilator combination, which combination is rollable as a single unit, with the ventilator being positioned within the footprint of the bed.

With reference to FIG. 4 there is illustrated a preferred embodiment of the ventilator cart of the present invention. The ventilator cart 150 includes an outermost rectangular base frame 151 which has sides 152, 153, 154 and 155. The cart 150 also includes an innermost rectangular support frame 156 which has sides 157, 158, 159 and 160. Innermost support frame 156 telescopes upwardly and downwardly with respect to the outermost base frame 151. The outermost frame 151 has fixedly secured thereto a pair of standards or uprights 161a and 161b, the lower ends of which are fixedly secured to frame sides 154 and 155, respectively. Fixedly secured to each standard 161a and 161b is a vertical slide 162, such as the type manufactured by Accuride (registered trademark).

Referring to FIG. 5, it can be seen that each vertical slide 162 includes a plate 163 which is fixedly secured to a mounting block 164 via fasteners 165. Plate 163 includes a pair of inwardly facing legs 163a. Block 164 is secured to the upper end of each of the standards 161a and 161b. Vertical slide 162 further includes a rail 166 which is mounted for vertical translational movement with respect to the plate 163 via a number of steel balls 167 held within a vertically slidable ball retainer 179. A strap 178 encircles the vertical extent of the ball retainer 179, has ends fixed to the rail 166 at a point approximately midway of the vertical extent of the rail 166, and is secured to the plate 163 at 163b. Balls 167 in retainer 179 ride between the outer sides of the legs 163a of plate 163 and inwardly turned portions 166a of rail 166. It will be appreciated that legs 163a, balls 167 and inwardly turned portions 166a effectively function as a linear ball bearing assembly. Rail 166 is itself secured to mounting bar 168 which is, in turn, secured to a ventilator (phantom lines) via appropriate hardware 169.

At the upper end of each mounting bar 168 there is an ear 170 which is attached to the upper end of an air or gas spring 171. The lower end of each mounting bar 168 is fixedly secured to the sides 159, 160, respectively, of the frame 156. At the lower ends of each air spring 171 there is provided a clevis 172 which is secured to the piston 173 of the air spring 171. The clevis 172 is pinned via a pin 174 to an ear 175 one of which is located at each forward corner 176, 177 of the outermost frame 151. Legs 180 are provided for securing casters 181 to the outermost frame 151.

A ventilator (phantom) to be secured to the ventilator cart 150 rests atop the innermost support frame 156 and is secured to the mounting bars 168 via the fasteners 169. The angled orientation of the gas springs 171 allows for proper vertical travel of a ventilator supported by the cart 150, while simultaneously allowing one to physically overcome the force of the gas springs in order to force the ventilator downwardly into a nested configuration without any undue difficulty.

In order to actuate the gas springs 171 to raise the ventilator from its lowered position to its raised position, there are provided a pair of levers 185 located beneath the forward side 152 of the outermost frame 151. Each lever 185 includes a dog leg portion 186 which can be actuated by a foot of a care provider. Dog leg section 186 is connected to a linear section 187 which terminates in a hooked portion 188. Hooked portion 188 is positioned directly underneath the actuating rod 190 of the gas spring 171. The levers 185 are supported within tabs secured to the side 152, such as that shown at 192. Downward movement of the dog leg section 186 of each lever 185 causes upward rotation of the hooked portion 188, which actuates the actuating rod 190 of the air spring thereby enabling a care provider to manually raise the ventilator aided of course by the upward thrust of the gas spring 171.

It will be appreciated that the ventilator cart described herein can be used in any number of applications where a particular piece of medical equipment is desired to be rollably transported and selectively raised and lowered. Therefore, the cart is not to be limited solely for use in conjunction with ventilators and is claimed to have application to any number of different types of medical equipment.

Those skilled in the art will readily recognize numerous adaptations and modifications which can be made to the present invention and which will result in an improved combination nestable mobile ventilator and critical care bed, yet all of which will be within the spirit and scope of the present invention as defined by the following claims. Therefore, I intend to be limited only by the appended claims and their equivalents.

What is claimed is:

1. The combination comprising:
   a hospital bed having a base, a patient support mounted on said base, and opposite head and foot ends, said base including wheels thereon;
   a ventilator supported on a cart, said cart including wheels thereon; and
   means for docking at least one of said ventilator and cart to said base of said bed, said ventilator and cart being positioned underneath said patient support and at one of said ends of said bed when said ventilator and said bed are removably secured together, said combination thereby being rollable as a unit.

2. The combination of claim 1 wherein said docking means includes means for preventing said patient support mounted on said base from being lowered onto said ventilator.

3. The combination of claim 1 wherein said bed defines a footprint on a floor surface therebelow by projecting downwardly thereon a periphery of said bed, and wherein said ventilator is positioned underneath said patient support and within said bed footprint when docked to said base.

4. The combination of claim 1 wherein said docking means includes means for powering said ventilator.

5. The combination of claim 1 wherein one of said base, ventilator and cart includes a power supply means for powering said ventilator.

6. The combination of claim 5 wherein said power supply means is mounted on said base.

7. The combination comprising:
   a hospital bed having a base, a patient support mounted on said base and opposite head and foot ends, said base including wheels thereon, said bed defining a footprint on a floor surface therebelow by projecting downwardly thereon a periphery of said bed; and
   a ventilator supported on a cart, said cart including wheels thereon, at least one of said ventilator and cart being dockable to said base whereby said ventilator and said bed may be removably secured together and rolled as a unit, said ventilator and cart being positioned underneath said patient support, at one of said ends of said bed and within said bed footprint.

8. The combination of claim 7 wherein one of said base, ventilator and cart includes a power supply means thereon for powering said ventilator.

9. The combination of claim 8 wherein said power supply means is mounted on said base.

10. The combination of claim 1 or claim 7 wherein said ventilator is positioned at said head end of said bed.

11. The combination of claim 1 or claim 7 wherein said hospital bed base is generally Y-shaped having a pair of spaced arms on one end thereof and said ventilator and cart are dockable to said base within said spaced arms.

12. The combination of claim 1 or claim 7 wherein said cart includes a selectively raisable and lowerable support for supporting said ventilator, whereby said ventilator may be lowered on said support for docking to said base beneath said patient support and said ventilator may be detached from said base and rollable to a position adjacent a side of said bed and raised by said support for care provider access thereto and manipulation thereof.

13. A combination comprising:
   a hospital bed having a base and a patient support mounted on said base, said base being generally Y-shaped having a pair of spaced arms on one end thereof, said base including wheels thereon, said bed defining a footprint on a floor surface therebelow by projecting downwardly thereon a periphery of said bed; and
   a ventilator on a cart, said cart including wheels thereon and a selectively raisable and lowerable support for supporting said ventilator, said ventilator and cart being dockable to said base within said spaced arms when said ventilator is lowered by said support whereby said ventilator and bed may be rolled as a unit, said ventilator being positioned underneath said patient support and within said bed footprint.

14. The combination of claim 13 wherein said ventilator is detachable from said base and rollable to a position adjacent a side of said bed whereby a care provider can raise said ventilator to provide the care provider with easy access to said ventilator for manipulation thereof.

15. The combination of claim 13 wherein said cart including said raisable and lowerable support comprises:
   a base frame, said wheels being mounted thereon;
   a pair of standards secured to said base frame on either side thereof;
   a vertical slide connected to each said standard;
   a support frame connected to said vertical slides;
   a pair of gas springs having first ends connected to said base frame and second ends connected to said vertical slides; and
   an actuator for actuating said gas springs whereby when actuated said gas springs provide lift assistance to a care provider in raising said ventilator from a lowered position to a raised position.

16. The combination of claim 15 wherein said actuator is foot actuated.

17. The combination of claim 15 wherein said actuator comprises:
a pair of rods rotatably mounted to said base frame, each of said rods including a foot actuatable pedal on one end and a lever on the other end, said lever being positioned adjacent an actuating pin of one of said gas springs, whereby when said pedal is depressed by a care provider's foot said rod rotates, driving said lever against said actuating pin of said gas spring.

* * * * *